(12) United States Patent
Noda et al.

(10) Patent No.: US 10,413,456 B2
(45) Date of Patent: Sep. 17, 2019

(54) ABSORBENT BODY AND ABSORBENT ARTICLE CONTAINING SAID ABSORBENT BODY

(71) Applicant: UNICHARM CORPORATION, Shikokuchuo-shi, Ehime (JP)

(72) Inventors: Yuki Noda, Kanonji (JP); Masashi Uda, Kanonji (JP); Takashi Maruyama, Kanonji (JP)

(73) Assignee: UNICHARM CORPORATION, Ehime (JP)

( * ) Notice: Subject to any disclaimer, the term of this patent is extended or adjusted under 35 U.S.C. 154(b) by 550 days.

(21) Appl. No.: 14/764,227

(22) PCT Filed: Apr. 10, 2014

(86) PCT No.: PCT/JP2014/060506
§ 371 (c)(1),
(2) Date: Jul. 29, 2015

(87) PCT Pub. No.: WO2014/199714
PCT Pub. Date: Dec. 18, 2014

(65) Prior Publication Data
US 2015/0366726 A1 Dec. 24, 2015

(30) Foreign Application Priority Data

Jun. 11, 2013 (JP) .................... 2013-122534
Mar. 31, 2014 (JP) .................... 2014-074557

(51) Int. Cl.
*A61F 13/15* (2006.01)
*A61F 13/20* (2006.01)
(Continued)

(52) U.S. Cl.
CPC ...... *A61F 13/533* (2013.01); *A61F 13/15203* (2013.01); *A61F 13/536* (2013.01);
(Continued)

(58) Field of Classification Search
CPC .. A61F 2013/530233; A61F 2013/5386; A61F 13/15203; A61F 13/533;
(Continued)

(56) References Cited

U.S. PATENT DOCUMENTS 4,847,141 A * 7/1989 Pazos ..................... A61F 13/53
442/364
5,085,914 A * 2/1992 Perdelwitz, Jr. ........ A47L 13/16
428/137
(Continued)

FOREIGN PATENT DOCUMENTS

CN 1859887 A 11/2006
EP 1348413 A1 10/2003
(Continued)

OTHER PUBLICATIONS

International Search Report dated May 20, 2014, corresponds to International Application No. PCT/JP2014/060506.

*Primary Examiner* — Michele M Kidwell
(74) *Attorney, Agent, or Firm* — Hauptman Ham, LLP

(57) ABSTRACT

An object of the present disclosure is to provide an absorbent body that is both soft and resistant to twisting. The absorbent body of the present disclosure is as follows. An absorbent body for an absorbent article includes thermoplastic resin fibers and cellulose-based water-absorbing fibers, at least some of the thermoplastic resin fibers have a first section 6' exposed on a surface of the liquid-permeable layer side of the absorbent body, a second section 6" exposed on a surface of the liquid-impermeable layer side of the absorbent body and a joint section 6''' connecting the first section 6' and second section 6", and the tensile strength in a thickness direction of the absorbent body is 100 Pa or greater.

18 Claims, 7 Drawing Sheets

(51) Int. Cl.
*A61F 13/533* (2006.01)
*A61F 13/536* (2006.01)
*A61L 15/60* (2006.01)
*A61L 15/22* (2006.01)
*A61F 13/53* (2006.01)
*A61F 13/539* (2006.01)

(52) U.S. Cl.
CPC .............. *A61L 15/225* (2013.01); *A61L 15/60* (2013.01); *A61F 2013/15292* (2013.01); *A61F 2013/15447* (2013.01); *A61F 2013/530007* (2013.01); *A61F 2013/530036* (2013.01); *A61F 2013/5395* (2013.01); *A61F 2013/530233* (2013.01); *A61F 2013/530386* (2013.01); *A61F 2013/53908* (2013.01); *A61L 2300/802* (2013.01)

(58) Field of Classification Search
CPC .......... A61F 13/536; A61F 2013/15292; A61F 2013/15447; A61F 2013/530007; A61F 2013/530036; A61F 2013/530386; A61F 2013/53908; A61F 2013/5395; A61L 15/60; A61L 15/225; A61L 2300/802; A61K 31/27
See application file for complete search history.

(56) References Cited

U.S. PATENT DOCUMENTS

| | | | |
|---|---|---|---|
| 5,154,714 A * | 10/1992 | Nomura | A61F 13/532 604/366 |
| 5,486,167 A * | 1/1996 | Dragoo | A61F 13/15203 604/358 |
| 5,653,702 A * | 8/1997 | Brohammer | A61F 13/53713 604/370 |
| 5,833,679 A | 11/1998 | Wada | |
| 5,904,971 A | 5/1999 | Anderson et al. | |
| 6,867,156 B1 * | 3/2005 | White | A61F 13/53436 428/119 |
| 2001/0056269 A1 | 12/2001 | Shimada et al. | |
| 2002/0019614 A1 | 2/2002 | Woon et al. | |
| 2002/0106478 A1 * | 8/2002 | Hayase | A47L 13/16 428/91 |
| 2002/0133131 A1 * | 9/2002 | Rangachari | A61F 13/15203 604/370 |
| 2003/0118764 A1 * | 6/2003 | Adams | A61F 13/535 428/36.91 |
| 2003/0187417 A1 * | 10/2003 | Kudo | A61F 13/15699 604/379 |
| 2004/0267220 A1 * | 12/2004 | Hull, Jr. | A61F 13/4756 604/380 |
| 2006/0030632 A1 * | 2/2006 | Krueger | A61L 15/225 521/50 |
| 2006/0058746 A1 | 3/2006 | Poccia et al. | |
| 2006/0141891 A1 | 6/2006 | Melius et al. | |
| 2007/0207309 A1 * | 9/2007 | Gonzales | A61L 15/225 428/327 |
| 2007/0255243 A1 | 11/2007 | Kaun et al. | |
| 2008/0183150 A1 | 7/2008 | Nanjyo et al. | |
| 2009/0043273 A1 | 2/2009 | Carlucci et al. | |
| 2009/0076473 A1 | 3/2009 | Kasai et al. | |
| 2009/0287174 A1 | 11/2009 | Carlucci et al. | |
| 2010/0178320 A1 * | 7/2010 | Westrin | A61L 15/32 514/1.1 |
| 2013/0018348 A1 | 1/2013 | Carlucci et al. | |
| 2014/0171894 A1 | 6/2014 | Detani et al. | |
| 2016/0101208 A1 * | 4/2016 | Topolkaraev | B29C 47/0011 604/370 |
| 2017/0128283 A1 * | 5/2017 | Uda | A61F 13/53 |

FOREIGN PATENT DOCUMENTS

| | | |
|---|---|---|
| EP | 2022452 A1 | 2/2009 |
| EP | 2123242 A1 | 11/2009 |
| JP | 8-71105 A | 3/1996 |
| JP | 2002-011047 A | 1/2002 |
| JP | 2004-073698 A | 3/2004 |
| JP | 2004-188077 A | 7/2004 |
| JP | 2004-535842 A | 12/2004 |
| JP | 2007-89907 A | 4/2007 |
| JP | 2008-513134 A | 5/2008 |
| JP | 2008-132056 A | 6/2008 |
| JP | 2008-231619 A | 10/2008 |
| JP | 2011-255023 A | 12/2011 |
| JP | 2012-192058 A | 10/2012 |
| JP | 2013-027664 A | 2/2013 |
| TW | 513300 B | 12/2002 |
| WO | 02/054977 A2 | 7/2002 |
| WO | 2004/024044 A1 | 3/2004 |
| WO | 2006/034096 A1 | 3/2006 |

\* cited by examiner

ABSORBENT BODY AND ABSORBENT ARTICLE CONTAINING SAID ABSORBENT BODY

RELATED APPLICATIONS

The present application is a National Phase of International Application Number PCT/JP2014/060506, filed Apr. 11, 2014, which claims priority to Japanese Application Number 2013-122534, filed Jun. 11, 2013 and to Japanese Application Number 2014-074557, filed Mar. 31, 2014.

TECHNICAL FIELD

The present invention relates to an absorbent body and to an absorbent article comprising the absorbent body.

BACKGROUND ART

An absorbent body for an absorbent article is known, which has an absorbent retaining layer comprising fluff pulp, a super-absorbent polymer and heat sealable synthetic resin fibers, and a nonwoven fabric layer composed of heat sealable synthetic resin fibers which is situated on the front sheet side of the absorbent retaining layer (PTL 1). In the absorbent body described in PTL 1, the heat sealable synthetic resin fibers in the absorbent retaining layer are tangled or heat-fused together, and the heat sealable synthetic resin fibers in the absorbent retaining layer and the heat sealable synthetic resin fibers in the nonwoven fabric layer are heat-fused, in order to prevent deformation of the absorbent body during use of the absorbent article.

CITATION LIST

Patent Literature

PTL 1 Japanese Unexamined Patent Publication No. 2002-11047

SUMMARY OF INVENTION

Technical Problem

In PTL 1, to prevent disintegration of the body fluid-absorbent retaining layer, it has a design that prevents twisting of the absorbent article by heat-fusion of the absorbent retaining layer and the nonwoven fabric layer at their contact surfaces, thereby improving the bonding strength between them, and heat fusion of the fusible synthetic resin fibers together in the absorbent retaining layer. With the absorbent article described in PTL 1, however, the degree of heat fusion is increased thereby impeding twisting of the absorbent article, but the absorbent article has also tended to become hard.

It is therefore an object of the present invention to provide an absorbent body that is both soft and resistant to twisting.

Solution to Problem

The present inventors have discovered an absorbent body for an absorbent article comprising a liquid-permeable layer, a liquid-impermeable layer and an absorbent body provided between the liquid-permeable layer and the liquid-impermeable layer, wherein the absorbent body includes thermoplastic resin fibers and cellulose-based water-absorbing fibers, at least some of the thermoplastic resin fibers have a first section exposed on a surface of the liquid-permeable layer side of the absorbent body, a second section exposed on a surface of the liquid-impermeable layer side of the absorbent body and a joint section connecting the first section and second section, and the tensile strength in a thickness direction of the absorbent body is 100 Pa or greater.

Advantageous Effects of Invention

The absorbent body of the invention is soft and resistant to twisting.

DESCRIPTION OF EMBODIMENTS

Definitions

"Exposed"

As used herein, the term "exposed" as it relates to thermoplastic resin fibers means that the thermoplastic resin fibers are present on the surface of the liquid-permeable layer side or the surface of the liquid-impermeable layer side of the absorbent body.

"Mean Fiber Length"

As used herein, the mean fiber length for non-pulp thermoplastic resin fibers and cellulose-based water-absorbing fibers, such as regenerated cellulose fibers or semisynthetic fibers, is measured according to JIS L 1015:2010, Appendix A, "A7.1 Measurement of Fiber Length", "A7.1.1 Method A (standard method) Method measuring individual fiber lengths on scaled glass plate".

This method is the test method corresponding to ISO 6989 published in 1981.

"Mean Fiber Length"

As used herein, the mean fiber length of pulp is the weight-weighted average fiber length, and it is the L(w) value measured using Kajaani fiber Lab fiber properties (off-line)] by Metso Automation.

"Melting Point"

As used herein, the term "melting point" of thermoplastic resin fibers refers to the peak top temperature for the endothermic peak during conversion from solid to liquid, upon measurement with a differential scanning calorimetry analyzer at a temperature-elevating rate of 10° C./min. The differential scanning calorimetry analyzer used may be, for example, a DSC-60-type DSC measuring apparatus by Shimadzu Corp.

The absorbent body of the present disclosure, and an absorbent article comprising the absorbent body, will now be described. The absorbent body of the present disclosure will be explained as being incorporated into an absorbent article, as necessary.

[Absorbent Body]

The absorbent body of the present disclosure comprises thermoplastic resin fibers and cellulose-based water-absorbing fibers. Also, in the absorbent body of the present disclosure, all or at least some of the thermoplastic resin fibers have a first section exposed on the surface on the liquid-permeable layer side of the absorbent body and a second section exposed on the surface of the liquid-impermeable layer side of the absorbent body, and a joint section connecting the first section and the second section.

Figure 1:
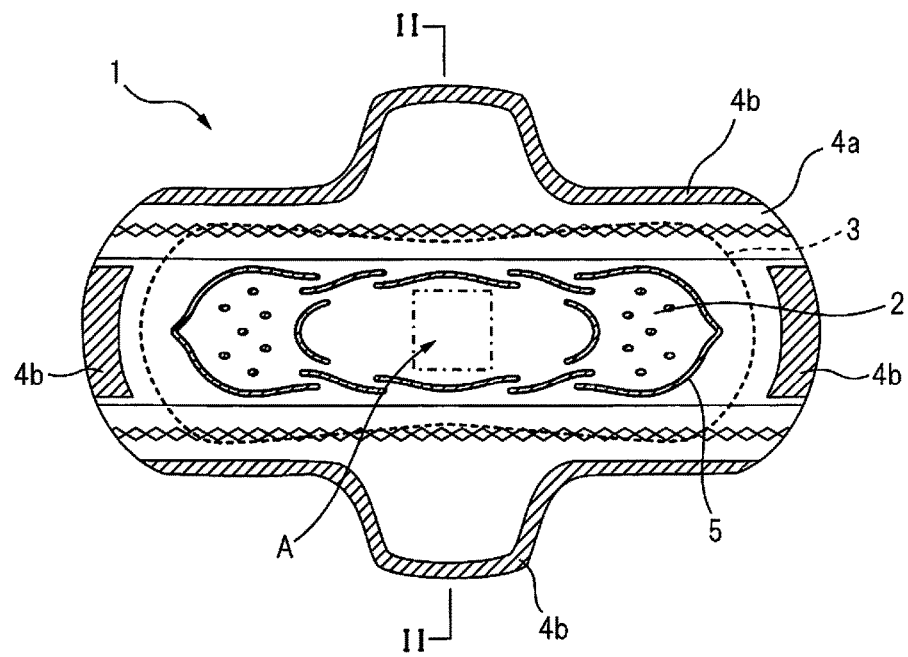
FIG. 1 is a plan view of an absorbent article, specifically a sanitary napkin, comprising an absorbent body according to one embodiment of the present disclosure.

FIG. 1 is a plan view of an absorbent article, specifically a sanitary napkin 1, comprising an absorbent body according to one embodiment of the present disclosure. The sanitary napkin 1 shown in FIG. 1 has its forward direction facing left in the drawing. The sanitary napkin 1 shown in FIG. 1 has a liquid-permeable top sheet 2 as the liquid-permeable layer, an absorbent body 3, and a liquid-impermeable back sheet as a liquid-impermeable layer (not shown).

FIG. 1 will now be explained in detail as it relates to the locations of the absorbent article described below.

Figure 2:
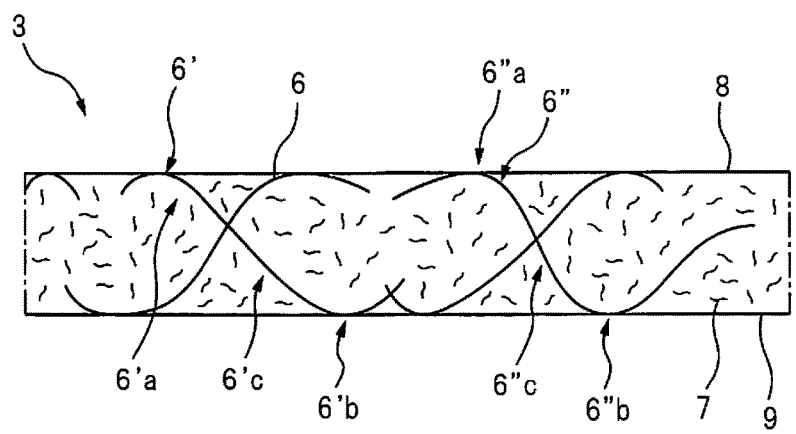
FIG. 2 is a cross-sectional view of section A of the sanitary napkin 1 shown in FIG. 1, along cross-section

FIG. 2 is a cross-sectional view of region A of the sanitary napkin 1 shown in FIG. 1, along cross-section II-II. For convenience in FIG. 2, only the absorbent body 3 is shown while the liquid-permeable layer and liquid-impermeable layer are omitted. The absorbent body 3 in FIG. 2 comprises thermoplastic resin fibers 6 and cellulose-based water-absorbing fibers 7. Also in FIG. 2, the thermoplastic resin fibers 6' each have a first section 6'a exposed on the surface 8 of the liquid-permeable layer side of the absorbent body 3 and a second section 6'b exposed on the surface 9 of the liquid-impermeable layer side of the absorbent body 3, and a joint section 6'c connecting the first section 6'a and the second section 6'b.

More specifically, the thermoplastic resin fibers 6' have, at one end (the left end), a first section 6'a exposed on the surface 8 on the liquid-permeable layer side of the absorbent body 3, at the other end (the right end), a second section 6'b exposed on the surface 9 on the liquid-impermeable layer side of the absorbent body 3, and a joint section 6'c connecting the first section 6'a and the second section 6'b. Also the thermoplastic resin fibers 6" have, at one end (the left end), a first section 6"a exposed on the surface 8 on the liquid-permeable layer side of the absorbent body 3, a second section 6"b exposed on the surface 9 on the liquid-impermeable layer side, between the one end (the left end) and the other end (the right end), and a joint section 6"c connecting the first section 6"a and the second section 6"b.

For explanation in FIG. 2, the thermoplastic resin fibers 6 are drawn thick and the cellulose-based water-absorbing fibers 7 are drawn thinner and shorter than the thermoplastic resin fibers 6, but this does not reflect the actual thicknesses and lengths of the fibers.

With the absorbent body of the present disclosure, wherein at least some of the thermoplastic resin fibers have a first section, a second section exposed on the surface on the liquid-impermeable layer side of the absorbent body and a joint section connecting the first section and second section, the thermoplastic resin fibers function as a lattice to hold the other components of the absorbent body, such as cellulose-based water-absorbing fibers, thereby improving the strength of the absorbent body. As a result, when the force of body pressure or the like is applied, there is less detachment inside the absorbent body, and the absorbent body (and absorbent article) becomes more resistant to twisting than an absorbent body containing no thermoplastic resin fibers, such as an absorbent body containing pulp alone.

Also, in the absorbent body of the present disclosure, at least some of the thermoplastic resin fibers have a first section and a second section exposed on the surface of the liquid-impermeable layer side of the absorbent body, and a joint section connecting the first section and the second section. Consequently, if the absorbent body in the absorbent article is bonded to a layer adjacent to the wearer side of the absorbent body (for example, a liquid-permeable layer) and/or a layer adjacent to the clothing side of the absorbent body (for example, a liquid-impermeable layer), detachment within the layers inside the absorbent body will occur less frequently and the absorbent body will thus be resistant to twisting. The reason for this will be explained in regard to the absorbent article.

In addition, the absorbent body described in PTL 1 is designed to prevent twisting of the absorbent body by heat-fusion of the fusible synthetic resin fibers. However, although it makes the absorbent body resistant to twisting, increasing the amount of heat-fusion also tends to harden the absorbent body.

In the absorbent body of the present disclosure, the strength of the absorbent body is increased without being dependent on heat fusion of the thermoplastic resin fibers, and it is therefore softer than the absorbent body described in PTL 1, and thus the person wearing the absorbent article is less likely to experience discomfort.

In the absorbent body of the present disclosure, the lower limit for the tensile strength in the thickness direction of the absorbent body is 100 Pa or greater, preferably 150 Pa or greater, more preferably 200 Pa or greater and even more preferably 250 Pa or greater. If the tensile strength is less than 100 Pa, the strength of the absorbent body will tend to be weak and the absorbent body will be more prone to twisting.

Furthermore, for the absorbent body of the present disclosure, the upper limit of the tensile strength in the thickness direction of the absorbent body is not particularly restricted but is preferably 3000 Pa or less from the viewpoint of softness.

Figure 8:
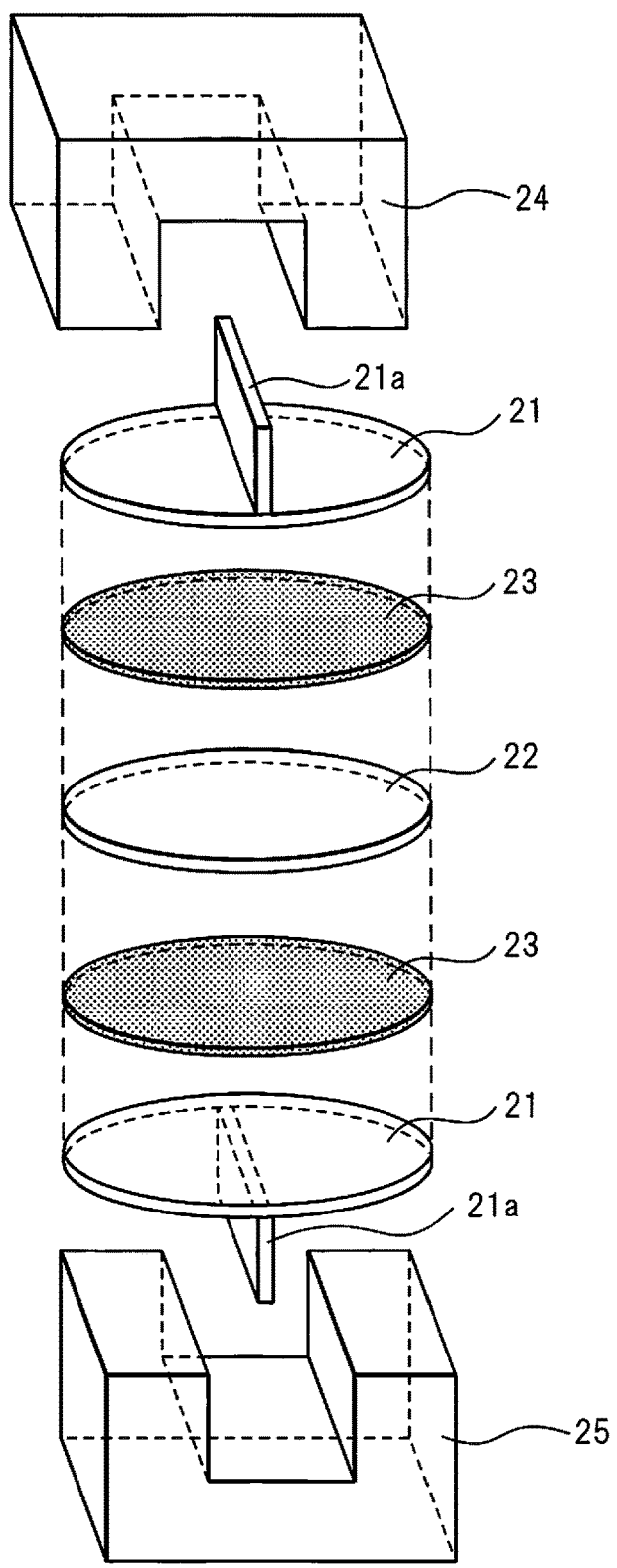
FIG. 8 is a diagram illustrating a method of measuring tensile strength.

As used herein, the tensile strength is measured as follows, using a device as shown in FIG. 8.

(1) A pair of acrylic jigs 21 (diameter: 68 mm, mass of each jig: 200 g, grip section 21a height: 50 mm) is prepared.

(2) A sample 22 with a diameter of 68 mm is prepared from the absorbent body.

(3) Two strips of double-sided tape 23 (3M Corp., adhesive transfer tape 950) cut out to a diameter of 68 mm are prepared.

(4) The sample 22 is affixed to the pair of jigs 21 using the two double-sided tape pieces 23, as shown in FIG. 8.

(5) The pair of jigs 21 with the sample 22 is placed on a holding stage 25, and a weight 24 (10.5 kg) is set over it and allowed to stand for 3 minutes.

(6) The pair of jigs 21 is set in a tensile tester (Shimadzu Corp., AG-1 kNI) with a grip spacing of 70 mm.

(7) The sample 22 is subjected to a tensile test at a speed of 100 mm/min until the inner layers of the sample 22 detach, and the maximum tensile force (N) at that time is recorded.

(8) The measurement is repeated a total of 5 times, the mean value of the maximum tensile force (N) is determined, and the tensile strength (Pa) is calculated by the following formula:

Tensile strength (Pa)=mean value (N) of maximum tensile force/0.003632 (m$^2$).

The measurement is conducted under 20° C. conditions.

In the absorbent body of the present disclosure, the thermoplastic resin fibers have mean fiber lengths that are preferably at least about two times, more preferably at least about 3 times, even more preferably at least about 4 times, yet more preferably at least about 5 times and even yet more preferably at least about 7 times the thickness of the absorbent body. If they are less than about two times the thickness, it will tend to be difficult for the thermoplastic resin fibers to be exposed both on the surface on the liquid-permeable layer side of the absorbent body and on the surface on the liquid-impermeable layer side of the absorbent body.

In the absorbent body of the present disclosure, the thermoplastic resin fibers have mean fiber lengths that are preferably about 30 times or less, more preferably about 20 times or less and even more preferably about 15 times or less the thickness of the absorbent body. If they are less than about 30 times the thickness, opening of the thermoplastic resin fibers will be insufficient and the uniformity of the absorbent body may be impaired.

In the absorbent body of the present disclosure, the thermoplastic resin fibers have mean fiber lengths of preferably about 6 to about 70 mm, more preferably about 10 to about 50 mm and even more preferably about 15 to about 40 mm. If the mean fiber lengths are less than about 6 mm, it will tend to be difficult for the thermoplastic resin fibers to be exposed both on the surface on the liquid-permeable layer side of the absorbent body and on the surface on the liquid-impermeable layer side of the absorbent body, and it will tend to be difficult for the thermoplastic resin fibers to become entangled with the other thermoplastic resin fibers and/or cellulose-based water-absorbing fibers.

Also, if the mean fiber lengths are greater than about 70 mm, the fiber-opening property of the thermoplastic resin fibers will be notably reduced and the absorbent body will include non-opened thermoplastic resin fibers, thus tending to lower the uniformity of the absorbent body.

This mean fiber length range is particularly preferred when the absorbent body of the present disclosure is mixed with cellulose-based water-absorbing fibers, such as pulp by an airlaid system.

In the absorbent body of the present disclosure, the thermoplastic resin fibers have a size of preferably about 0.5 to about 10 dtex and more preferably about 1.5 to about 5 dtex. If the size is less than about 0.5 dtex the opening property of the thermoplastic resin fibers may be reduced, and if the size exceeds 10 dtex the number of thermoplastic resin fibers will be smaller, tending to reduce the number of entangling points with the other thermoplastic resin fibers and/or cellulose-based water-absorbing fibers.

The absorbent body of the present disclosure will have a preferred thickness depending on the purpose of use of the absorbent body, but generally it will have a thickness of about 0.1 to about 15 mm, preferably about 1 to about 10 mm and more preferably about 2 to about 5 mm.

As used herein, the thickness (mm) of the absorbent body is that measured in the following manner.

An FS-60DS by Daiei Kagaku Seiki Mfg. Co., Ltd. is prepared [measuring surface: 44 mm (diameter), measuring pressure: 3 g/cm$^2$], five different locations of the absorbent body are pressed under standard conditions (temperature: 23±2° C., relative humidity: 50±5%), the thickness is measured after 10 seconds of pressing at each site, and the mean value of the five measured values is recorded as the thickness of the absorbent body.

The absorbent body of the present disclosure contains the thermoplastic resin fibers and cellulose-based water-absorbing fibers in proportions of preferably about 5 to about 50 parts by mass and about 50 to about 95 parts by mass, respectively, and more preferably about 10 to about 40 parts by mass and about 60 to about 90 parts by mass, respectively, based on their total of 100 parts by mass. If the proportion of thermoplastic resin fibers is less than about 5 parts by mass the strength of the absorbent body will tend to be insufficient and the absorbent body will be more prone to twisting, while if the proportion of thermoplastic resin fibers is greater than 50 parts by mass the liquid absorption property of the absorbent body will tend to be insufficient.

The absorbent body of the present disclosure has a basis weight of generally about 20 to about 1000 g/m$^2$, preferably about 50 to about 800 g/m$^2$ and more preferably about 100 to about 500 g/m$^2$. This is from the viewpoint of the strength and absorption property of the absorbent body.

The absorbent body of the present disclosure has a density of preferably about 0.06 to about 0.14 g/cm$^3$, more preferably about 0.07 to about 0.12 g/cm$^3$ and even more preferably about 0.08 to about 0.1 g/cm$^3$. If the absorbent body has the proportions of cellulose-based water-absorbing fibers and thermoplastic resin fibers specified above and the density specified above, the liquid absorption property of the absorbent body will tend to be excellent.

The density can be calculated from the basis weight and thickness of the absorbent body.

The basis weight is measured according to JIS L 1913: 2010 "6.2 Mass per unit area (ISO method)".

Also, from the viewpoint of the strength of connection between the absorbent body and the layer adjacent to the clothing side, such as a liquid-impermeable layer, the absorbent body of the present disclosure preferably has a flat surface, for example, a surface without ridge-furrows, on the liquid-impermeable layer side.

In the absorbent body of the present disclosure, the thermoplastic resin fibers are preferably not fused with cellulose-based water-absorbing fibers and/or other thermoplastic resin fibers. Also in the absorbent body of the present disclosure, the thermoplastic resin fibers are preferably entangled with cellulose-based water-absorbing fibers and/or the other thermoplastic resin fibers. This is because stiffness of the absorbent body itself will be prevented while the absorbent body will also deform (stretch) to some extent, minimizing interfacial peeling between the liquid-permeable layer and/or liquid-impermeable layer.

There is no particular limitation to an embossed section as described below.

For further increased strength, the absorbent body according to another embodiment of the present disclosure has a plurality of embossed sections that are formed by embossing the absorbent body and are situated at spacings.

Figure 3:
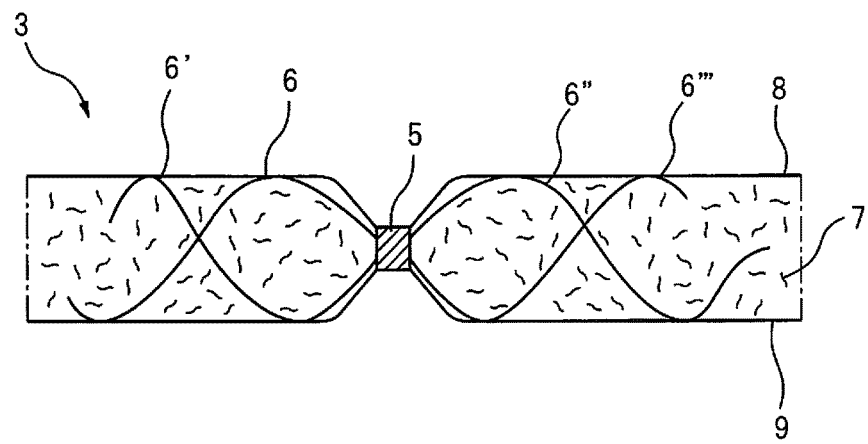
FIG. 3 is a cross-sectional view of section A of a sanitary napkin 1 according to another embodiment of the present disclosure, along cross-section II-II.

FIG. 3 is a cross-sectional view of this embodiment, which is a cross-sectional view corresponding to region A of the sanitary napkin 1 shown in FIG. 1, along cross-section II-II. In FIG. 3, only the absorbent body 3 is shown for convenience, while the liquid-permeable layer and liquid-impermeable layer are omitted. The sanitary napkin 1 shown in FIG. 3 is the same as the one shown in FIG. 2, except that it has a plurality of embossed sections (only one embossed section being shown in FIG. 3) formed by embossing the absorbent body 3 and situated at spacings.

In the absorbent body 3 shown in FIG. 3, one section of each of the thermoplastic resin fibers 6, 6', 6" and 6''' is incorporated in the embossed sections 5, and the thermoplastic resin fibers 6, 6', 6" and 6''' are connected through the embossed sections 5. Thus, the absorbent body 3 essentially contains thermoplastic resin fibers having longer mean fiber lengths than actual, the thermoplastic resin fibers 6, 6', 6" and 6''' have a higher function as a lattice for holding the other components of the absorbent body, such as cellulose-based water-absorbing fibers, than before being connected, and the strength of the absorbent body is increased.

In addition, since the embossed sections 5 partially anchor the thermoplastic resin fibers 6, 6', 6" and 6''', the fibers are resistant to movement even when body pressure or the like is applied, and the thermoplastic resin fibers 6, 6', 6" and 6''' are reliably anchored, such that the strength of the absorbent body is increased.

When the absorbent body of the present disclosure has a plurality of embossed sections, the thermoplastic resin fibers are preferably fused with the other fibers at the embossed sections. The effect described above will be more easily obtained by fusing the thermoplastic resin fibers with the other fibers, and especially the other heat-sealable fibers.

When the absorbent body of the present disclosure has a plurality of embossed sections, the thermoplastic resin fibers are preferably not fused with the cellulose-based water-absorbing fibers and/or the other thermoplastic resin fibers at the sections other than the embossed sections. If they are fused at the sections other than the embossed sections, the absorbent body will be resistant to twisting but will also tend to be hard.

When the absorbent body of the present disclosure has a plurality of embossed sections, the area ratio of the plurality of embossed sections with respect to the area of the absorbent body is preferably 1 to 20%, more preferably 2 to 15% and even more preferably 3 to 10%. If the area ratio is less than 1% the effect of the embossed sections will tend to be less apparent, and if the area ratio is greater than 10% the wearer will tend to feel the hardness of the absorbent body.

The terms "area of the absorbent body" and "area of the embossed sections" refer to the area when viewing the plane of the absorbent body.

When the absorbent body of the present disclosure has a plurality of embossed sections, the shapes of the embossed sections are not particularly restricted, and the embossed sections may be punctiform embossed sections or linear embossed sections. Examples of punctiform embossed sections include circular, elliptical, rectangular, triangular, star-shaped and heart-shaped sections.

There are no particular restrictions on the placement of the embossed sections, and for example, they may be placed in a zigzag fashion, such as in a square zigzag or 60° zigzag placement.

When the absorbent body of the present disclosure has a plurality of embossed sections, the spacing between the embossed sections is preferably 2.0 times or less the mean fiber length of the thermoplastic resin fibers, more preferably 1.0 times or less the mean fiber length of the thermoplastic resin fibers, even more preferably 0.7 times or less the mean fiber length of the thermoplastic resin fibers and yet more preferably 0.5 times or less the mean fiber length of the thermoplastic resin fibers. If the spacing is longer than 2.0 times the mean fiber length of the thermoplastic resin fibers, thermoplastic resin fibers anchored to different embossed sections will not become entangled and it will be difficult to increase the strength of the absorbent body. Also, if the spacing is 0.5 times or less the mean fiber length of the thermoplastic resin fibers, one thermoplastic resin fiber may become anchored to multiple embossed sections, thus helping to increase the strength of the absorbent body.

When the absorbent body of the present disclosure has a plurality of embossed sections, the area of each individual embossed section is preferably 0.1 to 20.0 mm$^2$, more preferably 1.0 to 15.0 mm$^2$ and even more preferably 2.0 to 10.0 mm$^2$. If the area is less than 0.1 mm$^2$ the protrusions of the embossing roll will be acute angles and the absorbent body may be torn, while if the area is greater than 20.0 mm$^2$ the absorbent body will tend to become hard.

Also, the absorbent body of the present disclosure preferably has a fiber density gradient that increases from the surface on the liquid-permeable layer side toward the surface on the liquid-impermeable layer side. Such a gradient will provide excellent softness on the liquid-permeable layer side while increasing fluid attraction on the liquid-impermeable layer side.

The thermoplastic resin fibers may be ones containing only a single component, such as simple fibers, or ones containing multiple components, such as composite fibers. Such components include polyolefins, such as polyethylene, polypropylene, polybutylene, ethylene-vinyl acetate copolymer, ethylene-ethyl acrylate copolymer, ethylene-acrylic acid copolymer and ionomer resins; polyesters, such as polyethylene terephthalate (PET), polybutylene terephthalate (PBT), polytrimethylene terephthalate (PTT) and polylactic acid; and polyamides, such as nylon.

Examples of composite fibers include composite fibers, such as core-sheath fibers, side-by-side fibers and sea/island fibers, and hollow type fibers; irregularly shaped fibers, such as flat fibers, Y-shaped fibers or C-shaped fibers; solid crimped fibers, such as latent crimped or developed crimped fibers, and split fibers that have been split by a physical load, such as a water stream, heat, embossing or the like, preferred among which are core-sheath fibers and especially PET/PE and PP/PE (core/sheath), which are industrially economical and highly safe.

The mass ratio of the core component/sheath component is preferably about 10/90 to about 90/10 and more preferably about 30/70 to about 70/30. If the sheath component proportion is low the fusibility will be reduced, and if the sheath component proportion increases, the spinnability will tend to be reduced.

Cellulose-based water-absorbing fibers may be pulp, such as wood pulp obtained using a conifer or broadleaf tree starting material, or nonwood pulp, such as bagasse, kenaf, bamboo, hemp, cotton (for example, cotton linter); regenerated cellulose fiber, such as rayon fiber, or semisynthetic fiber, such as acetate fiber. The pulp is preferably Kraft pulp which is industrially economical and highly safe.

The mean fiber lengths of the cellulose-based water-absorbing fibers are not particularly restricted. When the cellulose-based water-absorbing fibers are regenerated cellulose fibers or semisynthetic fibers, they may have mean fiber lengths of about 3 to about 70 mm, about 5 to about 50 mm or about 10 to about 40 mm. The regenerated cellulose fibers or semisynthetic fibers have the same function as thermoplastic resin fibers when dry, depending on their fiber lengths, and can provide the absorbent body with resistance to twisting.

The absorbent body of the present disclosure preferably further comprises a highly absorbent material. The absorbent body of the present disclosure comprises the highly absorbent material in a range of preferably about 5 to about 80 mass %, more preferably about 10 to about 60 mass % and even more preferably about 20 to about 40 mass % of the total mass of the absorbent body.

Examples of high-water-absorbing materials include starch-based, cellulose-based and synthetic polymer high-water-absorbing materials.

[Absorbent Article]

The absorbent article of the present disclosure comprises a liquid-permeable layer, a liquid-impermeable layer, and an absorbent body formed between the liquid-permeable layer and the liquid-impermeable layer.

The absorbent body in the absorbent article of the present disclosure is as follows.

In the absorbent article of the present disclosure, the cellulose-based water-absorbing fibers contained in the absorbent body are associated with the fluid absorption and fluid retention of the absorbent body while the thermoplastic resin fibers in the absorbent body are associated with connection between the liquid-permeable layer and/or liquid-impermeability, and especially the liquid-impermeable layer, and this prevents deformation of the absorbent article and imparts flexibility to the absorbent body and thus to the absorbent article.

Figure 4:
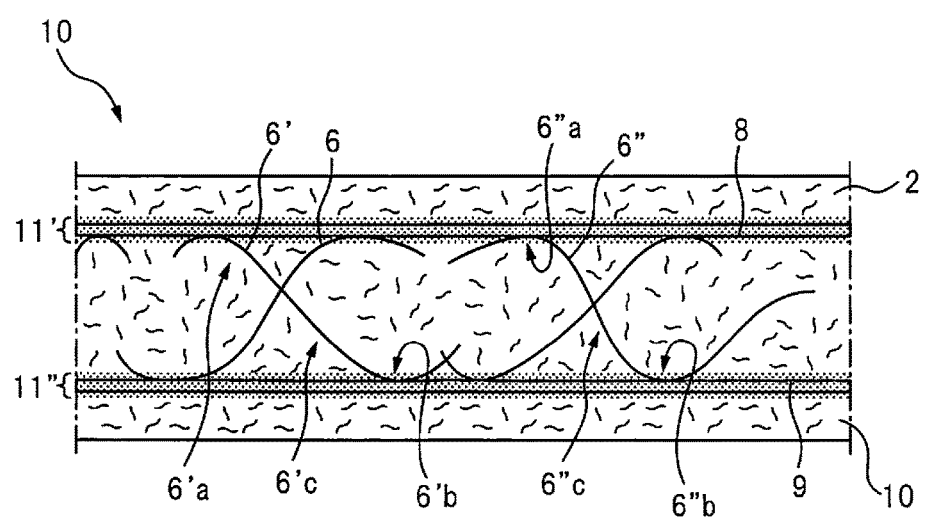
FIG. 4 is a cross-sectional view along cross-section II-II of FIG. 1.

FIG. 1 is a plan view of an absorbent article, specifically a sanitary napkin 1, comprising an absorbent body according to one embodiment of the present disclosure, and FIG. 4 is a cross-sectional view of FIG. 1 along cross-section II-II. The sanitary napkin 1 shown in FIG. 1 has its forward direction facing left in the drawing. The sanitary napkin 1 shown in FIG. 1 has a liquid-permeable top sheet 2 as the liquid-permeable layer, an absorbent body 3, and a back sheet as the liquid-impermeable layer (not shown). Also, the sanitary napkin 1 shown in FIG. 1 has a side sheet 4a, a seal section 4b that seals the edges of the sanitary napkin 1, and an embossed section 5 formed by embossing the top sheet 2 and absorbent body 3.

An absorbent article according to a different embodiment of the present disclosure does not have a side sheet, seal section and/or embossed section. An absorbent article according to yet another embodiment of the present disclosure has an auxiliary sheet between the top sheet and the absorbent body.

The sanitary napkin 1 shown in FIG. 4 has an adhesive section 11' between the top sheet 2 and the absorbent body 3 to connect the top sheet 2 and absorbent body 3, and an adhesive section 11" between the absorbent body 3 and the back sheet 10 to connect the absorbent body 3 and back sheet 10.

In the sanitary napkin 1 shown in FIG. 4, the first sections 6'a and 6"a that are each exposed on the surface 8 on the liquid-permeable layer side of the thermoplastic resin fibers 6' and 6", respectively, are connected to the layer adjacent to the wearer side, i.e. the top sheet 2, through the adhesive section 11'.

In the absorbent article of the present disclosure, as shown in FIG. 4, the first sections of the thermoplastic resin fibers that are exposed on the surface on the liquid-permeable layer side, being connected to the layer adjacent to the wearer side (for example, the liquid-permeable layer) through the adhesive section, produce more rigid connection between the absorbent body and the layer adjacent to the wearer side (for example, the liquid-permeable layer), and when the article is worn, they result in less detachment between the absorbent body and the layer adjacent to the wearer side and render the absorbent body and absorbent article less likely to undergo twisting.

Also, in the sanitary napkin 1 shown in FIG. 4, the second sections 6'b and 6"b each exposed on the surface 9 on the liquid-impermeable layer side of the thermoplastic resin fibers 6' and 6", respectively, are connected to the layer adjacent to the clothing side, i.e. the back sheet 10, through the adhesive section 11".

In the absorbent article of the present disclosure, as shown in FIG. 4, the second sections of the thermoplastic resin fibers that are exposed on the surface on the liquid-impermeable layer side, being connected to the layer adjacent to the clothing side (for example, the liquid-impermeable layer) through the adhesive section, produce rigid connection between the absorbent body and the layer adjacent to the clothing side (for example, the liquid-impermeable layer), and when the article is worn, they result in less detachment between the absorbent body and the layer adjacent to the clothing side and render the absorbent body and absorbent article less likely to undergo twisting.

Furthermore, in the embodiment shown in FIG. 4, the layer adjacent to the wearer side of the absorbent body (for example, the liquid-permeable layer) and the layer adjacent to the clothing side of the absorbent body (for example, the liquid-impermeable layer) are rigidly connected with the joint sections of the thermoplastic resin fibers through two adhesive sections, and therefore the absorbent body is resistant both to interlayer separation with the layer adjacent to the wearer side (for example, the liquid-permeable layer) and to separation within layers inside the absorbent body, thereby resulting in resistance to twisting of the absorbent body and the absorbent article.

The adhesive sections can be formed with an adhesive known in the technical field, without any particular restrictions.

The adhesive can be formed by a coating method, such as spiral coating application, coater application, curtain coater application or summit-gun coating.

Figure 5:
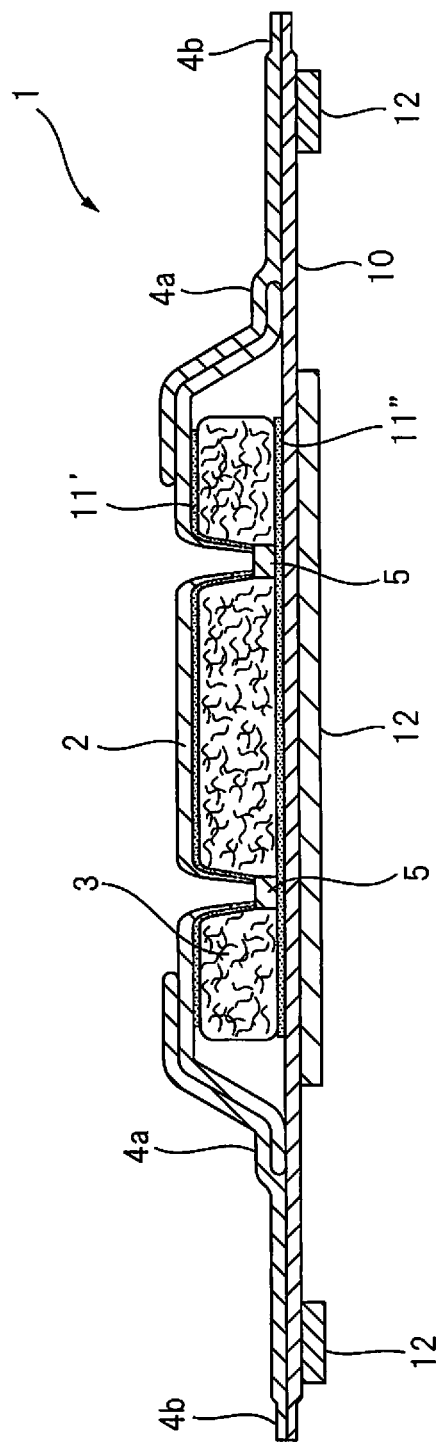
FIG. 5 is a cross-sectional view of the sanitary napkin 1 shown in FIG. 1, along cross-section II-II.

FIG. 5 is a cross-sectional view of the sanitary napkin 1 shown in FIG. 1, along cross-section II-II. The sanitary napkin 1 shown in FIG. 5 has a liquid-permeable top sheet 2 as the liquid-permeable layer, an absorbent body 3, a back sheet 10 as the liquid-impermeable layer, a side sheet 4a and a seal section 4b. Also, the sanitary napkin 1 shown in FIG. 5 has, on the surface on the clothing side of the back sheet 10, a pressure-sensitive adhesive section 12 for anchoring of the sanitary napkin 1 to clothing.

The sanitary napkin 1 shown in FIG. 5 comprises an adhesive section 11' for connection between the absorbent body 3 and top sheet 2, which is the layer adjacent to the wearer side, provided between the absorbent body 3 and the top sheet 2. Also, the sanitary napkin 1 shown in FIG. 5 comprises an adhesive section 11" for connection between the absorbent body 3 and back sheet 10, which is the layer adjacent to the clothing side, provided between the absorbent body 3 and the back sheet 10. The sanitary napkin 1 shown in FIG. 5 also has a plurality of embossed sections 5 formed by embossing the top sheet 2 and the absorbent body 3 with the adhesive section 11' between them.

Incidentally, the thermoplastic resin fibers and cellulose-based water-absorbing fibers are not shown separately for the absorbent body 3 shown in FIG. 5.

In the absorbent article of the present disclosure, the pressure-sensitive adhesive section can be formed by a pressure-sensitive adhesive known in the technical field.

When the absorbent article of the present disclosure has embossed sections formed by embossing at least the liquid-permeable layer and absorbent body, as shown in FIG. 5, connection between the liquid-permeable layer and absorbent body is more rigid and it is more resistant to twisting under application of body pressure.

Figure 6:
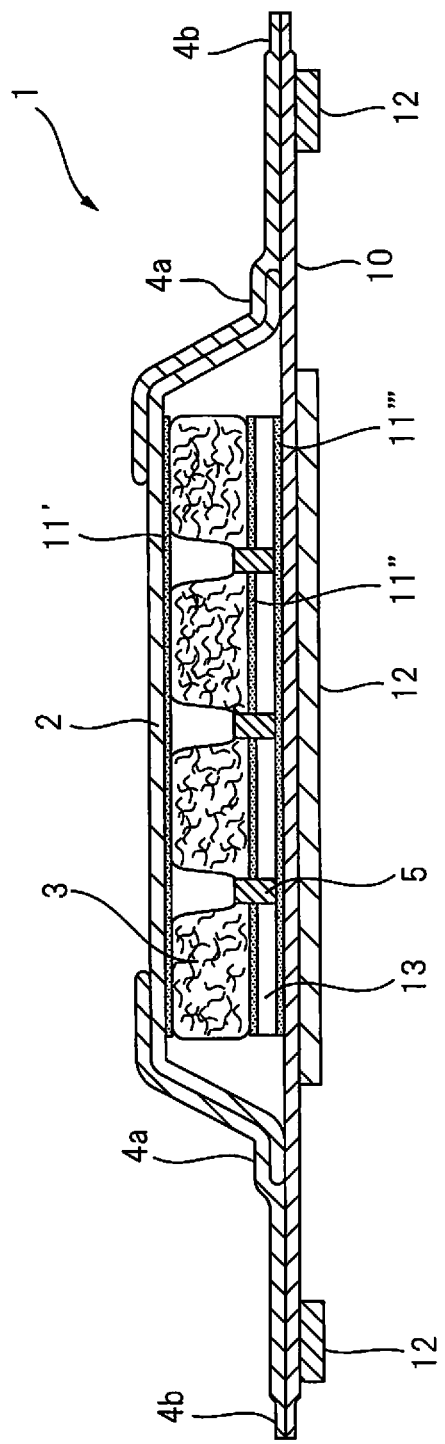
FIG. 6 is a cross-sectional view of an absorbent article according to another embodiment of the present disclosure.

FIG. 6 is a cross-sectional view of an absorbent article according to another embodiment of the present disclosure. FIG. 6 is a cross-sectional view of FIG. 1 along cross-section II-II.

The sanitary napkin 1 shown in FIG. 6 has a top sheet 2 as the liquid-permeable layer, an absorbent body 3, a back sheet 10 as the liquid-impermeable layer, a nonwoven fabric layer 13 between the absorbent body 3 and the back sheet 10, a side sheet 4a, and a seal section 4b. Also, the sanitary napkin 1 shown in FIG. 6 has, on the surface on the clothing side of the back sheet 10, a pressure-sensitive adhesive section 12 for anchoring of the sanitary napkin 1 to clothing.

The sanitary napkin 1 shown in FIG. 6 comprises an adhesive section 11' for connection between the absorbent body 3 and top sheet 2, which is the layer adjacent to the wearer side, provided between the absorbent body 3 and the top sheet 2. Also, the sanitary napkin 1 shown in FIG. 6 comprises an adhesive section 11" for connection between the absorbent body 3 and back sheet 10, provided between the absorbent body 3 and the nonwoven fabric layer 13 which is the layer adjacent to the clothing side. Also, the sanitary napkin 1 shown in FIG. 6 comprises an adhesive section 11''' provided between the nonwoven fabric layer 13 and the back sheet 10, for connection between them.

The sanitary napkin 1 shown in FIG. 6 also has a plurality of embossed sections 5 formed by embossing the absorbent body 3 and the nonwoven fabric layer 13, with the adhesive section 11" between them.

Incidentally, the thermoplastic resin fibers and cellulose-based water-absorbing fibers are not shown separately for the absorbent body 3 in FIG. 6.

When the absorbent article of the present disclosure has a nonwoven fabric layer between the absorbent body and the liquid-impermeable layer, as shown in FIG. 6, and the nonwoven fabric layer is a nonwoven fabric layer having a flat surface on the liquid-impermeable layer side, it is possible to rigidly connect the absorbent body to the liquid-impermeable layer with the surfaces sandwiching the flat nonwoven fabric layer. Furthermore, by providing an adhesive section between the absorbent body and the nonwoven fabric layer to connect them, it is possible to render connection between the absorbent body and the liquid-impermeable layer even more rigid.

In addition, if the absorbent body has embossed sections formed by embossing the absorbent body and the liquid-impermeable layer with the nonwoven fabric layer between them, the thermoplastic resin fibers of the absorbent body and the fibers of the nonwoven fabric will become entangled, thereby firmly connecting them and rendering the absorbent article resistant to twisting.

The absorbent article according to another embodiment of the present disclosure has a nonwoven fabric layer between the absorbent body and the liquid-impermeable layer, and the absorbent body is connected to the nonwoven fabric layer through the adhesive section.

Examples for the liquid-permeable layer include nonwoven fabrics, woven fabrics, fluid permeation hole-formed synthetic resin films and meshed net-like sheets, with nonwoven fabrics being preferred.

The liquid-impermeable layer is a sheet that does not allow permeation of liquid excreta of the user, and it is provided on the side in contact with the clothing (underwear) of the wearer to prevent leakage of liquid excreta that has been absorbed in the absorbent body. The liquid-impermeable layer is preferably moisture-permeable in addition to being liquid-impermeable, in order to reduce mustiness when worn.

Examples for the liquid-impermeable layer include waterproof treated nonwoven fabrics, films of synthetic resins (such as polyethylene, polypropylene and polyethylene terephthalate), composite sheets comprising nonwoven fabrics and synthetic resin films (such as composite films having an air permeable synthetic resin film bonded to a spunbond or spunlace nonwoven fabric), and SMS nonwoven fabrics comprising a highly water-resistant meltblown nonwoven fabric sandwiched between high-strength spunbond nonwoven fabrics.

[Production Method]

The absorbent body of the present disclosure may be produced by any method without any restrictions so long as it includes thermoplastic resin fibers and cellulose-based water-absorbing fibers, at least some of the thermoplastic resin fibers having a first section exposed on the surface of the liquid-permeable layer side of the absorbent body and a second section exposed on the surface of the liquid-impermeable layer side of the absorbent body, and any method known in the technical field may be utilized. The absorbent article of the present disclosure may also be produced by a method known in the technical field, except that it contains the absorbent body described above.

A production example for the absorbent article of the present disclosure will now be explained.

Figure 7:
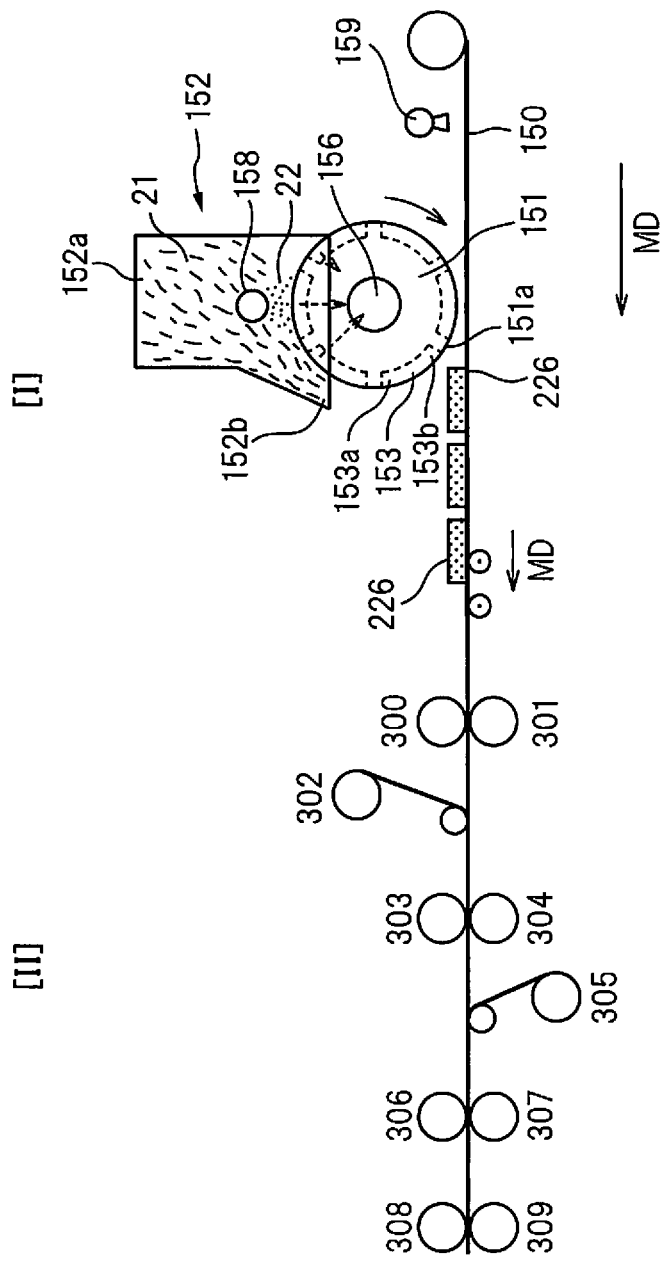
FIG. 7 is a diagram illustrating a method for producing an absorbent body and absorbent article according to an embodiment of the present disclosure.

FIG. 7 is a diagram illustrating a method for producing an absorbent body and an absorbent article according to an embodiment of the present disclosure. The method illustrated in FIG. 7 comprises a first step (I) and a second step (II).

Incidentally, the thermoplastic resin fibers and cellulose-based water-absorbing fibers are not shown separately in FIG. 7.

[First Step (I)]

A plurality of recesses 153 are formed at a prescribed pitch on the peripheral surface 151a of a suction drum 151 rotating in the machine direction MD, extending from the peripheral surface 151a toward the center of the suction drum, as a molding form in which the absorbent body material is to be packed. When the suction drum 151 is rotated and the recesses 153 approach the material feeder 152, the suction action of the suction section 156 causes the absorbent body material supplied from the material feeder 152 to accumulate in the recesses 153.

The material feeder 152, equipped with a hood 152a, is formed so as to cover the suction drum 151, and the material feeder 152 supplies a mixture 21 comprising cellulose-based water-absorbing fibers and thermoplastic resin fibers into the recesses 153 by air transport. The material feeder 152 is also provided with a particle feeder 158 that supplies super-absorbent polymer particles 22, so that super-absorbent polymer particles 22 are supplied to the recesses 153. The mixture 21 of the cellulose-based water-absorbing fibers and thermoplastic resin fibers and the super-absorbent polymer particles 22 (hereunder referred to as "absorbent body starting material") accumulates in the recesses 153 in a mixed state, and an absorbent body 226 is formed in the recesses 153.

In order for at least some of the thermoplastic resin fibers to have a first section exposed on the surface on the liquid-permeable layer side of the absorbent body, a second section exposed on the surface on the liquid-impermeable layer side of the absorbent body and a joint section connecting the first section and the second section (hereunder also referred to as "specified orientation"), the hood 152*a* of the material feeder 152 has an accumulation space 152*b* that is larger than hoods generally used in the technical field, at the downstream end in the machine direction MD (upstream from accumulation of the absorbent body starting material).

This will tend to cause the thermoplastic resin fibers to accumulate in the depthwise direction of the recesses 153, or in other words, in the direction from the peripheral surface 151*a* of the suction drum 151 toward the center.

As regards the absorbent body starting material and the recesses 153, the absorbent body starting material tends to accumulate in order from the recess section 153*a* of the recess at the downstream end of rotation of the suction drum toward the recess section 153*b* at the upstream end of rotation, and therefore the thermoplastic resin fibers tend to have the aforementioned specified orientation.

In addition, during accumulation of the absorbent body starting material in the recesses 153, the thermoplastic resin fibers can be easily given the aforementioned specified orientation by increasing the suction force of the suction drum upstream from accumulation of the absorbent body starting material, so that it is greater than downstream from accumulation of the absorbent body starting material.

Furthermore, if the rotational speed of the suction drum is slower than the rate of flow of the absorbent body starting material, the thermoplastic resin fibers will more easily adopt the aforementioned specified orientation.

Next, the absorbent body 226 formed in the recesses 153 is transported onto a carrier sheet 150 having an adhesive coated by a coating machine 159.

The carrier sheet 150 later forms a nonwoven fabric layer between the absorbent body and the liquid-impermeable layer, but in an embodiment where the absorbent article does not have a nonwoven fabric layer, the liquid-permeable layer, the liquid-impermeable layer or an optional auxiliary sheet or the like may be used as the carrier sheet.

[Second Step (II)]

The second step (II) is the same as a common step for producing a sanitary napkin. A pair of rolls 300, 301 punch out the absorbent body 226 obtained in the first step, into a prescribed shape. A liquid-permeable layer is supplied from a roll 302 and sealed with embossers 303, 304 having a high compression section and a low compression section, and the liquid-permeable layer and absorbent body 226 become integrated. Next, a liquid-impermeable layer 305 is supplied, and with the absorbent body 226 sandwiched between a liquid-permeable layer and liquid-impermeable layer, the product perimeter is subjected to embossing for sealing and passed to the seal section-forming steps 306 and 307, and finally cut into the product shape by steps 308 and 309.

As an example of the embossing step, a liquid-permeable layer and liquid-impermeable layer may be passed together between a patterned embossing roll, with patterned raised sections, and a flat roll, for embossing (a method known as round sealing). By heating the embossing roll and/or flat roll by this method, each sheet is softened so that the seal sections become more distinct. Examples of emboss patterns include lattice-like patterns, zigzag patterns and wavy patterns. In order to impede bending of the absorbent article at the borders of the seal sections, the emboss pattern is preferably intermittently elongated.

The temperature of the embossing roll during the embossing step is preferably in a prescribed relationship above the melting point of the thermoplastic resin fibers composing the absorbent body. Specifically, the temperature may be a temperature at which some of the thermoplastic resin fibers melt, and for example, when the thermoplastic resin fibers are sheath/core composite fibers, the temperature may be a temperature at or above the temperature at which partial melting of the sheath component begins.

The temperature for the embossing roll in the embossing step will usually be about 80° C. to about 160° C. and preferably about 120° C. to about 160° C., the pressure will usually be about 10 to about 3000 N/mm and preferably about 50 to about 500 N/mm, and the processing time will usually be about 0.0001 to about 5 seconds and preferably about 0.005 to about 2 seconds.

EXAMPLES

The invention will now be further explained by examples, with the understanding that the invention is not limited to the examples.

Production Example 1

An apparatus as illustrated in FIG. 7 was used to obtain an absorbent body comprising pulp and thermoplastic resin fibers in a mass ratio of 85:15, having a basis weight of 250 g/m$^2$ and a size of 50 mm length×25 mm width. The thermoplastic resin fibers were core-sheath fibers with a core of polyethylene terephthalate and a sheath of polyethylene, and having a mean fiber length of 30 mm and a size of 2.2 dtex.

Next, the absorbent body was passed between a pair of embossing rolls to form embossed sections in the absorbent body. The embossing rolls were a pin embossing roll having pin embossed sections with diameters of 1 mm arranged in a square zigzag fashion in the MD direction, and with center distances of 10 mm×10 mm (MD direction×CD direction) between the pin embossed sections, and a plain roll.

A polyethylene sheet (basis weight: 23 g/m$^2$) was cut to a size of 50 mm length×25 mm width to obtain a back sheet. Next, a hot-melt adhesive was coated onto the back sheet in a spiral fashion at a basis weight of 5 g/m$^2$, and then the absorbent body was layered over it with the plain roll-contacting surface facing the back sheet side, to obtain sample No. 1 for detachment testing.

Production Examples 2 to 4

Sample Nos. 2 to 4 for detachment testing were produced by the same procedure as Production Example 1, except that the mean fiber length of the thermoplastic resin fibers and the proportion of thermoplastic resin fibers and pulp were changed as shown in Table 1.

Production Example 5

Sample No. 5 for detachment testing was produced by the same procedure as Production Example 1, except that an SMS nonwoven fabric (basis weight: 13 g/m$^2$) was prepared as the nonwoven fabric layer, the absorbent body and SMS nonwoven fabric were layered with a spiral-coated hot-melt adhesive (basis weight: 5 g/m$^2$) between them, and the layered absorbent body and SMS nonwoven fabric were passed between a pair of embossing rolls, layering an absorbent body to sandwich the SMS nonwoven fabric.

Production Example 6

Sample No. 6 for detachment testing was produced according to Production Example 1, except that the mixture of pulp and thermoplastic resin fibers was changed to pulp (basis weight: 250 g/m$^2$) alone.

Examples 1 to 5 and Comparative Example 1

Samples No. 1 to No. 6 for detachment testing were evaluated for interfacial peeling between the absorbent body and the back sheet (the SMS nonwoven fabric for No. 6). The test procedure was as follows.

A tensile tester (AG-1kNI by Shimadzu Corp.) was prepared in a steady temperature and humidity room (temperature: 20° C., humidity: 60%), and set with an initial jig spacing of 20 mm between the upper jig and lower jig.

The edges of the detachment test sample (50 mm length× 25 mm width) in the lengthwise direction were preliminarily detached between the absorbent body and the back sheet across a length of 25 mm, and the absorbent body section was affixed to the upper jig while the back sheet section was affixed to the lower jig. Next, a load was applied to the detachment test sample at a pull rate of 100 mm/min, until the detachment test sample completely separated, and the displacement (mm) during maximum load was evaluated. The displacement is the value of the jig spacing (mm) during maximum load after subtracting 20 mm as the initial jig spacing.

The results are shown in Table 1. The thickness of each absorbent body is also shown in Table 1.

Production Example 7

An apparatus as illustrated in FIG. 7 was used to obtain an absorbent body comprising pulp and thermoplastic resin fibers in a mass ratio of 80:20, having a basis weight of 250 g/m$^2$ and a size of 50 mm length×25 mm width. The thermoplastic resin fibers were core-sheath fibers with a core of polyethylene terephthalate and a sheath of polyethylene with a melting point of 130° C., and having a mean fiber length of 30 mm and a size of 2.2 dtex.

Next, the absorbent body was passed between a pair of embossing rolls to obtain absorbent body No. 1 having embossed sections. The embossing rolls were a pin embossing roll having pin embossed sections with diameters of 3.0 mm arranged in a square zigzag fashion in the MD direction, and with center distances of 11 mm×11 mm (MD direction× CD direction) between the pin embossed sections, and a plain roll.

The embossing roll temperature was 110° C., the pressure was 1.73 kPa/mm$^2$ and the embossing time was 20 seconds.

For absorbent body No. 1, the embossed sections each had an area of about 7.1 mm$^2$, the area ratio of the embossed sections was 11.7%, and the embossed section spacing was 8 mm.

Production Example 8

Absorbent body No. 2 was formed according to Production Example 7, except that the pair of embossing rolls was

TABLE 1

| No. | Sample No. | Absorbent body basis weight (g/m$^2$) | Mass ratio[1] | Pulp basis weight (g/m$^2$) | Thermoplastic resin fibers Basis weight (g/m$^2$) | Thermoplastic resin fibers Mean fiber length (mm) | Displacement at maximum load (mm) | Absorbent body thickness (mm) |
|---|---|---|---|---|---|---|---|---|
| Example 1 | 1 | 250 | 85:15 | 212 | 38 | 30 | 2.1 | 3.0 |
| Example 2 | 2 | 250 | 95:5 | 237 | 13 | 30 | 1.4 | 2.9 |
| Example 3 | 3 | 250 | 95:5 | 237 | 13 | 5 | 1.2 | 3.0 |
| Example 4 | 4 | 250 | 50:50 | 125 | 125 | 30 | 2.4 | 3.1 |
| Example 5 | 5 | 250 | 85:15 | 212 | 38 | 30 | 2.8 | 3.1 |
| Comp. Example 1 | 6 | 250 | 100:0 | 250 | — | — | 0.8 | 3.1 |

[1]Mass ratio of pulp:thermoplastic resin fibers

From Table 1 it is seen that detachment test samples No. 1 to No. 5 had greater displacements during maximum load compared to layered product No. 6 which contained no thermoplastic resin fibers, and were therefore resistant to interlayer separation between the absorbent body and back sheet.

It is believed that detachment test samples No. 1 to No. 5 had greater displacements than detachment test sample No. 6 which contained no thermoplastic resin fibers, because at least some of the thermoplastic resin fibers in detachment test samples No. 1 to No. 5 had a first section exposed on the surface on the liquid-permeable layer side of the absorbent body, a second section exposed on the surface on the liquid-impermeable layer side of the absorbent body and a joint section connecting the first section and the second section.

changed to a pair of plain rolls (room temperature), and no embossed sections were formed.

Production Examples 9 to 12

Absorbent bodies Nos. 3 to 6 were obtained according to Production Example 7, except that the composition was changed as shown in Table 2.

Examples 6 to 10 and Comparative Example 2

Figure 9:
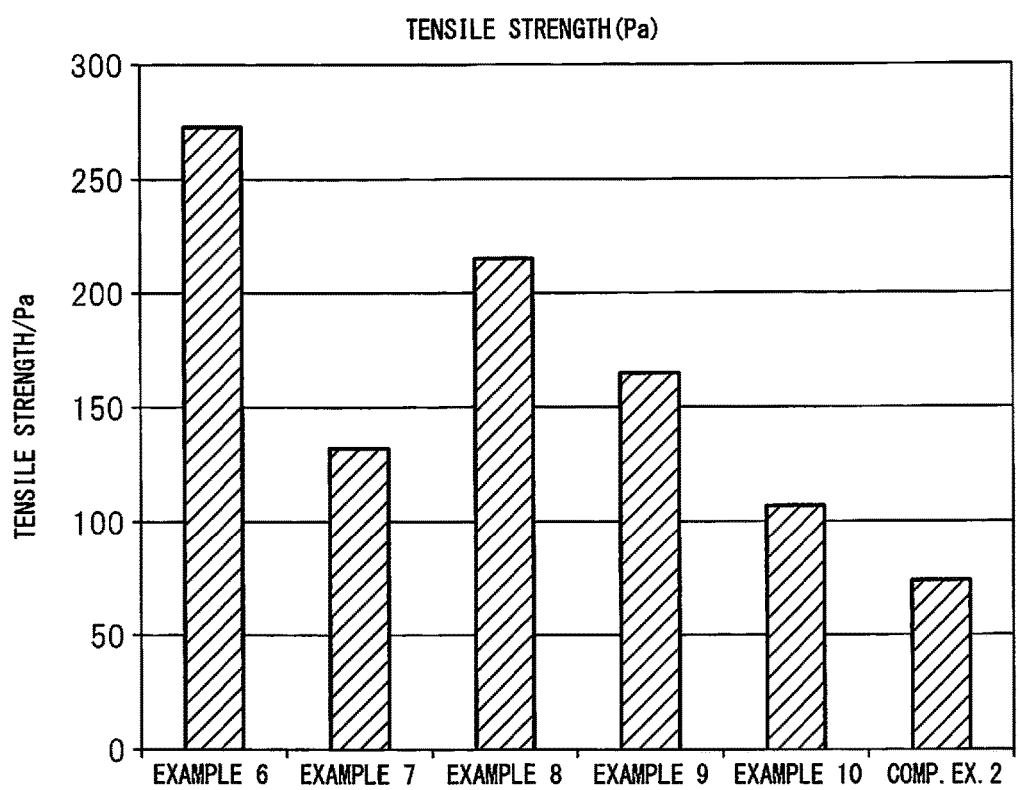
FIG. 9 is a diagram showing the results of an example.

The thicknesses and tensile strengths of absorbent bodies Nos. 1 to 6 are shown in Table 2, and their proportion (ratio of the embossed section spacing to the mean fiber length of the thermoplastic resin fibers) and tensile strengths are shown in FIG. 9.

TABLE 2

| No. | Absorbent body No. | Absorbent body thickness (mm) | Absorbent body basis weight (g/m²) | Embossed sections Present | Embossed sections Ratio[1] | Pulp basis weight (g/m²) | Thermoplastic resin fibers Basis weight (g/m²) | Thermoplastic resin fibers Mean fiber length (mm) | Tensile strength (Pa) |
|---|---|---|---|---|---|---|---|---|---|
| Example 6 | 1 | 3.0 | 240 | Yes | 0.27 | 200 | 40 | 30 | 273 |
| Example 7 | 2 | 3.2 | 240 | No | 0.27 | 200 | 40 | 30 | 132 |
| Example 8 | 3 | 3.0 | 240 | Yes | 0.40 | 200 | 40 | 20 | 215 |
| Example 9 | 4 | 3.0 | 240 | Yes | 0.67 | 200 | 40 | 12 | 165 |
| Example 10 | 5 | 3.0 | 240 | Yes | 1.33 | 200 | 40 | 6 | 107 |
| Comp. Example 2 | 6 | | 240 | No | — | 240 | 0 | — | 74 |

[1]Embossed section spacing/thermoplastic resin fiber mean fiber length

Based on Table 2 and FIG. 9 it is seen that longer fiber lengths of the thermoplastic resin fibers, and embossing of the absorbent body, results in higher tensile strength.

The present disclosure relates to the following J1 to J17.

[J1]
An absorbent body for an absorbent article comprising a liquid-permeable layer, a liquid-impermeable layer and an absorbent body provided between the liquid-permeable layer and the liquid-impermeable layer,
wherein the absorbent body includes thermoplastic resin fibers and cellulose-based water-absorbing fibers,
at least some of the thermoplastic resin fibers have a first section exposed on a surface of the liquid-permeable layer side of the absorbent body, a second section exposed on a surface of the liquid-impermeable layer side of the absorbent body and a joint section connecting the first section and second section, and
the tensile strength in a thickness direction of the absorbent body is 100 Pa or greater.

[J2]
The absorbent body according to J1, wherein the thermoplastic resin fibers have mean fiber lengths that are at least two times a thickness of the absorbent body.

[J3]
The absorbent body according to J1 or J2, wherein the thermoplastic resin fibers have mean fiber lengths of 6-70 mm.

[J4]
The absorbent body according to any one of J1 to J3, wherein the thermoplastic resin fibers are not fused with the cellulose-based water-absorbing fibers and/or other thermoplastic resin fibers.

[J5]
The absorbent body according to any one of J1 to J3, wherein the absorbent body has a plurality of embossed sections that are formed by embossing the absorbent body and are situated with spacings.

[J6]
The absorbent body according to J5, wherein the spacings are 2.0 times or less the mean fiber length of the thermoplastic resin fibers.

[J7]
The absorbent body according to J5 or J6, wherein the area ratio of the plurality of embossed sections with respect to the area of the absorbent body is 1% to 20%.

[J8]
The absorbent body according to any one of J5 to J7, wherein the thermoplastic resin fibers are not fused with the cellulose-based water-absorbing fibers and/or other thermoplastic resin fibers at the sections other than the embossed sections.

[J9]
The absorbent body according to any one of J1 to J8, wherein the absorbent body contains the thermoplastic resin fibers and cellulose-based water-absorbing fibers in proportions of 5-50 parts by mass and 50-95 parts by mass, respectively, based on their total of 100 parts by mass.

[J10]
The absorbent body according to any one of J1 to J9, which has a fiber density gradient that increases from the surface on the liquid-permeable layer side toward the surface on the liquid-impermeable layer side.

[J11]
An absorbent article comprising a liquid-permeable layer, a liquid-impermeable layer, and the absorbent body according to any one of J1 to J10 provided between the liquid-permeable layer and the liquid-impermeable layer.

[J12]
The absorbent article according to J11, wherein the absorbent article comprises an adhesive section between the absorbent body and the layer adjacent to the wearer side, for connection between the absorbent body and the layer adjacent to the wearer side, and the first sections of the thermoplastic resin fibers are connected to the layer adjacent to the wearer side through the adhesive section.

[J13]
The absorbent article according to J11 or J12, wherein the absorbent article comprises an adhesive section between the absorbent body and a layer adjacent to a clothing side, for connection between the absorbent body and the layer adjacent to the clothing side, and the second sections of the thermoplastic resin fibers are connected to the layer adjacent to the clothing side through the adhesive section.

[J14]
The absorbent article according to any one of J11 to J13, wherein the absorbent article has embossed sections formed by embossing at least the liquid-permeable layer and the absorbent body.

[J15]
The absorbent article according to any of J11 to J14, wherein the absorbent article has a nonwoven fabric layer between the absorbent body and the liquid-impermeable layer, and the absorbent article has an adhesive section between the absorbent body and the nonwoven fabric layer, for connection between the absorbent body and the nonwoven fabric layer.

[J16]
The absorbent article according to J15, wherein the absorbent article has embossed sections formed by embossing at least the absorbent body and the nonwoven fabric layer.

[J17]
An absorbent body for an absorbent article comprising a liquid-permeable layer, a liquid-impermeable layer and an absorbent body provided between the liquid-permeable layer and the liquid-impermeable layer,
wherein the absorbent body includes thermoplastic resin fibers and cellulose-based water-absorbing fibers,
the thermoplastic resin fibers have mean fiber lengths of 6-70 mm, and
the tensile strength in the thickness direction of the absorbent body is 100 Pa or greater.

The present disclosure further relates to the following K1 to K5.

[K1]
An absorbent body for an absorbent article comprising a liquid-permeable layer, a liquid-impermeable layer and an absorbent body provided between the liquid-permeable layer and the liquid-impermeable layer,
wherein the absorbent body includes thermoplastic resin fibers and cellulose-based water-absorbing fibers,
the thermoplastic resin fibers have mean fiber lengths of 6-70 mm, and
the tensile strength in the thickness direction of the absorbent body is 100 Pa or greater.

[K2]
The absorbent body according to K1, wherein the thermoplastic resin fibers have mean fiber lengths that are at least two times a thickness of the absorbent body.

[K3]
The absorbent body according to K1 or K2, wherein the thermoplastic resin fibers have mean fiber lengths of 6-70 mm.

[K4]
The absorbent body according to any one of K1 to K3, wherein the thermoplastic resin fibers are not fused with the cellulose-based water-absorbing fibers and/or other thermoplastic resin fibers.

[K5]
The absorbent body according to any one of K1 to K3, wherein the absorbent body has a plurality of embossed sections that are formed by embossing the absorbent body and are situated with spacings.

[K6]
The absorbent body according to K5, wherein the spacings are 2.0 times or less the mean fiber length of the thermoplastic resin fibers.

[K7]
The absorbent body according to K5 or K6, wherein the area ratio of the plurality of embossed sections with respect to the area of the absorbent body is 1% to 20%.

[K8]
The absorbent body according to any one of K5 to K7, wherein the thermoplastic resin fibers are not fused with the cellulose-based water-absorbing fibers and/or other thermoplastic resin fibers at the sections other than the embossed sections.

[K9]
The absorbent body according to any one of K1 to K8, wherein the absorbent body contains the thermoplastic resin fibers and cellulose-based water-absorbing fibers in proportions of 5-50 parts by mass and 50-95 parts by mass, respectively, based on their total of 100 parts by mass.

[K10]
An absorbent article comprising a liquid-permeable layer, a liquid-impermeable layer, and the absorbent body according to any one of K1 to K9 provided between the liquid-permeable layer and the liquid-impermeable layer.

REFERENCE SIGNS LIST

1 Sanitary napkin
2 Top sheet
3 Absorbent body
4a Side sheet
4b Seal section
5 Embossed section
6 Thermoplastic resin fiber
6a First section
6b Second section
6c Joint section
7 Cellulose-based water-absorbing fiber
8 Surface on liquid-permeable layer side
9 Surface on liquid-impermeable layer side
10 Back sheet
11',11" Adhesive sections
12 Pressure-sensitive adhesive section
13 Nonwoven fabric layer
21 Jig
22 Sample
23 Double-sided tape
24 Weight
25 Holding stage

The invention claimed is:
1. An absorbent body for an absorbent article comprising a liquid-permeable layer, a liquid-impermeable layer and an absorbent body provided between the liquid-permeable layer and the liquid-impermeable layer,
wherein
    the absorbent body includes thermoplastic resin fibers and cellulose-based water-absorbing fibers,
    at least some of the thermoplastic resin fibers have
        a first section exposed on a surface of a liquid-permeable layer side of the absorbent body,
        a second section exposed on a surface of a liquid-impermeable layer side of the absorbent body, and
        a joint section connecting the first section and second section,
    a tensile strength in a thickness direction of the absorbent body is 100 Pa or greater, and
    the thermoplastic resin fibers have mean fiber lengths of 6-70 mm.

2. The absorbent body according to claim 1, wherein the thermoplastic resin fibers have the mean fiber lengths that are at least two times a thickness of the absorbent body.

3. The absorbent body according to claim 1, wherein the thermoplastic resin fibers are not fused with the cellulose-based water-absorbing fibers and/or other thermoplastic resin fibers.

4. The absorbent body according to claim 1, wherein the absorbent body has a plurality of embossed sections that are formed by embossing the absorbent body and are situated with spacings.

5. The absorbent body according to claim 4, wherein the spacings are 2.0 times or less the mean fiber length of the thermoplastic resin fibers.

6. The absorbent body according to claim 4, wherein an area ratio of the plurality of embossed sections with respect to an area of the absorbent body is 1% to 20%.

7. The absorbent body according to claim 4, wherein the thermoplastic resin fibers are not fused with the cellulose-based water-absorbing fibers and/or other thermoplastic resin fibers other than at the embossed sections.

8. The absorbent body according to claim 1, wherein the absorbent body contains the thermoplastic resin fibers and cellulose-based water-absorbing fibers in proportions of 5-50 parts by mass and 50-95 parts by mass, respectively, based on a total of 100 parts by mass.

9. The absorbent body according to claim 1, wherein the absorbent body has a fiber density gradient that increases from the surface on the liquid-permeable layer side toward the surface on the liquid-impermeable layer side.

10. An absorbent article comprising a liquid-permeable layer, a liquid-impermeable layer, and the absorbent body according to claim 1 provided between the liquid-permeable layer and the liquid-impermeable layer.

11. The absorbent article according to claim 10, further comprising an adhesive section between the absorbent body and a layer adjacent to a wearer side of the absorbent body, for connection between the absorbent body and the layer adjacent to the wearer side of the absorbent body,
wherein the first sections of the thermoplastic resin fibers are connected to the layer adjacent to the wearer side of the absorbent body through the adhesive section.

12. The absorbent article according to claim 10, further comprising an adhesive section between the absorbent body and a layer adjacent to a clothing side of the absorbent body, for connection between the absorbent body and the layer adjacent to the clothing side of the absorbent body,
wherein the second sections of the thermoplastic resin fibers are connected to the layer adjacent to the clothing side of the absorbent body through the adhesive section.

13. The absorbent article according to claim 10, wherein the absorbent article has embossed sections formed by embossing at least the liquid-permeable layer and the absorbent body.

14. The absorbent article according to claim 10, further comprising:
a nonwoven fabric layer between the absorbent body and the liquid-impermeable layer, and
an adhesive section between the absorbent body and the nonwoven fabric layer, for connection between the absorbent body and the nonwoven fabric layer.

15. The absorbent article according to claim 14, wherein the absorbent article has embossed sections formed by embossing at least the absorbent body and the nonwoven fabric layer.

16. An absorbent body for an absorbent article comprising a liquid-permeable layer, a liquid-impermeable layer and an absorbent body provided between the liquid-permeable layer and the liquid-impermeable layer,
wherein
the absorbent body includes thermoplastic resin fibers and cellulose-based water-absorbing fibers,
the thermoplastic resin fibers have mean fiber lengths of 6-70 mm, and
a tensile strength in the thickness direction of the absorbent body is 100 Pa or greater.

17. An absorbent article comprising a liquid-permeable layer, a liquid-impermeable layer, and the absorbent body according to claim 16 provided between the liquid-permeable layer and the liquid-impermeable layer,
wherein
the absorbent article further comprises an adhesive section between the absorbent body and a layer adjacent to a wearer side of the absorbent body, for connection between the absorbent body and the layer adjacent to the wearer side of the absorbent body, and
first sections of the thermoplastic resin fibers are connected to the layer adjacent to the wearer side of the absorbent body through the adhesive section.

18. The absorbent body according to claim 16, wherein the tensile strength in the thickness direction of the absorbent body is not greater than 3000 Pa.

* * * * *